United States Patent [19]
Webb et al.

[11] Patent Number: 6,000,800
[45] Date of Patent: Dec. 14, 1999

[54] COAXIAL SPATIALLY RESOLVED REFRACTOMETER

[75] Inventors: Robert H. Webb, Lincoln; Stephen A. Burns, Reading, both of Mass.; Carl Murray Penney, Saratoga Springs, N.Y.

[73] Assignee: Schepens Eye Research Institute, Boston, Mass.

[21] Appl. No.: 09/102,699

[22] Filed: Jun. 22, 1998

[51] Int. Cl.[6] .................................................. A61B 3/10
[52] U.S. Cl. ............................................................ 351/211
[58] Field of Search .................................... 351/205, 206, 351/207, 208, 211, 212, 221, 215; 600/473, 476; 356/128, 131, 132

[56] References Cited

U.S. PATENT DOCUMENTS

| | | | |
|---|---|---|---|
| 5,258,791 | 11/1993 | Penney et al. | 351/211 |
| 5,873,832 | 2/1999 | Maloney et al. | 351/207 |
| 5,875,019 | 2/1999 | Villani | 351/211 |

*Primary Examiner*—George Manuel
*Attorney, Agent, or Firm*—Lahive & Cockfield, LLP

[57] ABSTRACT

A refractometer provides a reference path coaxial with a measurement path and thereby simplifies construction by reducing the number of parts and simplifies maintenance by halving the number of optical axes to be aligned. The refractometer includes a reference projector for projecting a reference pattern on a reference pattern position on a detector during a reference interval, a site-selector for selecting a measurement site on an optical system, and a measurement projector for projecting a measurement pattern through this selected measurement site and onto a measurement pattern position on the detector during a measurement interval. The reference projector, the site selector, and the measurement projector are all aligned along the same optical axis. In the case in which the optical system is a human eye, the designated site in typically a site on the cornea and the detector is the retina of the eye. The refractometer provides an aligner for alignining the reference pattern position with a measurement pattern position. The amount by which these two positions are moved in order to achive alignment provides a measure of the optimal wavefront corresponding to the measurement site.

51 Claims, 12 Drawing Sheets

COAXIAL SPATIALLY RESOLVED REFRACTOMETER

This invention relates to the field of instrumentation for optical measurements and, in particular, to instruments for determining the direction of the vector normal to the optimal wavefront at selected points of an optical system. An optimal wavefront of an optical system is that wavefront which is brought to an optimal focus by the optical system. In the case of an ideal optical system, the optimal wavefront is a planar wavefront.

BACKGROUND

The action of an optical system can be considered as a transformation that operates on an incident wavefront to generate a transmitted wavefront. In many optical systems, different points on the wavefront experience different transformations depending on what portions of the optical system they traverse. For example, when a wave is incident on a lens, those portions of the wavefront that traverse the periphery of the lens will experience phase delays which differ from those experienced by those portions of the wavefront that illuminate the center of the lens. Since a wavefront is a locus of points having constant phase, this results in a transmitted wavefront having a shape that differs from that of the incident wavefront. By appropriately shaping and positioning lenses, one can conform the shape of the output wavefront of an optical system to a desired shape.

In some cases, an optical system is known to produce an incorrect transformation and the optical designer's role is to design a second optical system to correct that deficiency. For example, in the case of a human eye requiring a corrective lens, the optical components of the human eye perform an optical transformation that is imperfect. In another example, one might inadvertently install a flawed objective lens in a large telescope. Rather than attempting to replace the objective lens, it may be preferable to install a corrective lens. In both of these cases, it is useful for the designer of corrective lenses to know the nature of the flawed optical transformation.

An optical transformation can be pictured as a change in the shape of the wavefront. For example, FIG. 12A shows an optical system in which an incident plane wave is transformed into a spherical wave. The system in FIG. 12A is therefore representative of a human eye which does not require corrective lenses.

FIG. 12B shows an optical system representative of a human eye in need of correction. In contrast to the system of FIG. 12A, this system shows a planar wavefront transformed into an irregular wavefront. The eye's inability to bring this irregular wavefront into focus on the retina causes the perceived image to appear distorted or blurred.

FIG. 12C shows the optical system of FIG. 12B but with an "optimal wavefront" incident on the system. The shape of this optimal wavefront is chosen such that the transformation provided by the optical system in FIG. 12B results in a spherical wavefront instead of the irregularly shaped wavefront shown in FIG. 12B. It is apparent from comparison of FIGS. 12A and 12C that a corrective optical system which transforms an incident wavefront into this optimal wavefront before the wave undergoes the flawed optical transformation has the effect of correcting for the flawed optical transformation.

By fitting the wavefront normal vector at selected points on the wavefront, one can determine the shape of the wavefront. Using this wavefront, one can then design an optical system that corrects for the flawed optical transformation.

A common method for measuring the optical characteristics of a human eye is a simple substitution technique of placing lenses having different correction factors in front of the eye and asking the patient whether or not the overall image has improved. Using this method, a clinician can determine an overall correction for the optical characteristics of the eye. The instrument that is typically used to approximate an optical system that corrects for the flawed optical transformation of an eye is referred to as a "refractometer." In the case of a general lens system, corrections are determined by a variety of tests, each referred to by its own name, such as the "Foucault test." Throughout this specification, the term "refractometer" will be used to refer to all of the instruments that make such tests.

The simple substitution technique determines the overall correction for the eye, but it is limited to prismatic, cylindrical, and spherical corrections. These corrections provide only the lower-order terms of the Siedel or polynomial model of the eye's optical system. The foregoing method does not correct for the errors that are specified by higher-order terms of the Siedel or polynomial model. Additionally, it is not possible, using this method, to obtain point-by-point measurements of the optimal wavefront's normal vector at designated sites on an optical system having spatial extent. For example, where the optical system is a cornea, it is not possible, using this method, to determine the optimal wavefront's normal vector at each point on the cornea A number of refractometers have been developed that are designed to determine the optimal wavefront at designated sites on an optical system. For example, Penney U.S. Pat. No. 5,258,791, incorporated herein by this reference, describes an optical system including a reference optical subsystem for projecting a reference pattern on the patient's retina through a reference area on the cornea and a separate measurement optical subsystem for projecting a measurement pattern on the patient's retina through a measurement area on the cornea.

To determine the shape of the optimal wavefront at a designated site on the cornea using the refractometer disclosed in Penney, the measurement pattern is moved across the retina until its location coincides with the location of the reference pattern. Based on the difference between the initial and final positions of the measurement pattern, the refractometer disclosed in Penney can infer the direction of the vector normal to the optimal wavefront at the selected corneal site.

A disadvantage of the device disclosed in Penney is, simply put, that it has far too many parts. As a result, it is costly to acquire, complex to assemble, and requires frequent alignment during operation. What is therefore desirable in the art is a refractometer that provides the functionality of the Penney refractometer at reduced cost and complexity and without the need for frequent alignment.

SUMMARY

A refractometer according to the invention provides a reference path that is coaxial with a measurement path. This feature of the invention simplifies construction by reducing the number of parts and simplifies maintenance by halving the number of optical axes to be aligned.

In a refractometer embodying the invention, two spatial light pattern generators are aligned along a common optical axis. The term "spatial light pattern generator" is used throughout this specification to refer to any device that changes a property of light, such as brightness, according to a spatially variable pattern. As used herein, spatial light pattern generators include holes in an opaque masking material, electronically addressable transmissive or reflective arrays, and light sources having controllable brightness patterns.

The first spatial light pattern generator is optically conjugate to a measurement plane at which the optimal wavefront's normal vector is to be determined. This measurement plane can be made coplanar with a pupil of the lens system, a pupil or cornea of an eye, or a similar structure whose optical properties are of interest. The second spatial light pattern generator is optically conjugate to a detector plane on which a detector spatially responsive to light source can be placed. Such a detector can be a CCD array, a quadrant detector, or the retina of an eye. In optical design terminology, a plane is often used to refer to the apical position of a surface. It is in this sense that the term "plane" is used throughout this specification.

A controller coupled to the first and second spatial light pattern generators operates the refractometer in two time intervals: a measurement interval, and a reference interval. During the measurement interval, the measurement pattern is projected through a selected measurement site on the measurement plane, and, ultimately, to a measurement pattern position on the detector plane. During the reference interval, a reference pattern is projected through a generally different site, referred to as the "selected reference site," on the measurement plane and onto a generally different reference pattern position on the detector plane. The measurement interval and the reference interval can be made to alternate rapidly enough so that, as a result of persistence of vision, the measurement pattern and the reference pattern appear to be projected simultaneously. Alternatively, the measurement interval and the reference interval can be temporally overlapping or, in the limit, be contemporaneous.

The refractometer of the invention further includes an image aligner for controlling the location of the measurement pattern during the measurement interval. By operation of the aligner, the measurement pattern can be moved relative to the reference pattern. The distance and direction that the measurement pattern is moved in order to align it with the reference pattern on the detector plane provides a measure of the normal vector of the optimal wavefront at the measurement plane.

The refractometer can further include lenses that make the detector plane optically conjugate to a reference plane at which the reference pattern is generated and to an object plane, at which the measurement pattern is generated. Other, or the same, lenses in the refractometer can make the measurement plane optically conjugate to a site-selection plane at which the sites or areas on the measurement plane used during the reference and measurement intervals are selected.

A refractometer embodying this invention consists of two optical subsystems aligned along substantially the same optical axis: a reference optical subsystem and a measurement optical subsystem. The reference optical subsystem projects a reference pattern onto a reference pattern position on a detector plane through a selected reference site on the measurement plane. The measurement optical subsystem projects a measurement pattern onto a measurement pattern position on the detector plane through a selected measurement site on the measurement plane. The two subsystems may have some or all of their elements in common. The fact that the two subsystems are aligned along the same optical axis is a distinguishing feature of this invention. A second distinguishing feature of this invention is that the subsystems may be temporally rather than spatially distinct. In the case in which the optical system to be evaluated is a human eye, the measurement plane can be at the cornea or pupil and the detector can be the retina of the eye.

In a preferred embodiment, the location of the measurement pattern on the detector can be controllede by an observer through the use of an optical aligner coupled to the measurement optical subsystem. Using this optical aligner, the observer can move the measurement pattern on the detector until it is aligned with the reference pattern on the detector. The distance and the direction in which the observer moves the measurement pattern in order to align it with the reference pattern provide a measure of the shape of the optimal wavefront associated with the portion of the wave incident on the selected measurement site on the measurement plane. In the case in which the optical system is the human eye, the observer is typically the patient. However, the observer can also be an automatic computer processor that is coupled to a detector that observes the retina and that can determine the relative locations of the reference pattern and the measurement pattern on the retina.

In both embodiments of the invention disclosed herein, a first spatial light pattern generator functions as a moveable aperture and a second spatial light pattern generator functions as a moveable light source. In the first embodiment, the moveable aperture is conjugate to the measurement plane and the moveable light source is conjugate to the detector plane. The second embodiment reverses this. In the second embodiment, it is the moveable aperture that conjugate to the detector plane and the moveable light source that is conjugate to the measurement plane.

A reference optical subsystem for practice of the invention can include a spatial light pattern generator located at a reference plane conjugate to the detector plane and a light source for illuminating that spatial light pattern generator. Where the optical system is the eye, the detector is a retina and the reference plane is a proximal retinal conjugate plane. In the first embodiment, the reference optical subsystem can include a clear plate on which is engraved a reticle and a light source for illuminating the reticle. In this first embodiment, the measurement interval and the reference interval can be contemporaneous. In the second embodiment, the first spatial light pattern generator generates both reference and measurement light patterns in alternating time intervals, and the second spatial light pattern generator selects both the reference and measurement sites in the corresponding time intervals.

In the first embodiment, the site-selecting spatial light pattern generator provides a small aperture mask or light source that can be moved, under the control of a processor such as a computer, to selected positions in a site-selection plane. This site-selection plane is optically conjugate to a measurement plane on which is disposed the optical system whose optimal wavefront is sought. Where the optical system is the eye, the measurement plane is coplanar with the cornea or pupil. Where the optical system is a non-living lens system, the measurement plane can be coplanar with the pupil of the lens system.

Because the site-selection plane and the measurement plane are conjugates, all light emanating from a selected point on the site-selection plane is directed to a corresponding point on the measurement plane. Since each point on the site-selection plane corresponds to a point on the measurement plane, when the site selector moves the mask or light source to a particular location on the site-selection plane, it also selects a measurement site on the measurement plane. This has the effect of selecting a measurement site on the cornea or pupil of the eye, or on the pupillary plane of the lens system.

In the first embodiment, the site selector can be implemented as a moveable aperture on the site-selection plane operating in conjunction with a light source behind the aperture. In the second embodiment, the site selector can be implemented as a small, moveable light source on the site-selection plane.

The optical measurement subsystem for either embodiment of the invention includes a light source or mask on an object plane optically conjugate to the detector plane. Where the optical system is the eye, the object plane can be optically conjugate to the retina of the eye. Where the optical system is a lens system, the object plane can be optically conjugate to a detector at the lens system's image plane. In the second embodiment, the light source can be formed by addressing selected light modulating elements in a spatial light pattern generator on the object plane in a manner that forms a small aperture through which light from a light source can pass. In the first embodiment, the light source can be formed directly by providing a spatial light pattern generator and by either addressing selected areas of the spatial light pattern generator.

Where the optical system to be evaluated is a system of lenses, the refractometer is as described above but with the retinal conjugate plane replaced by a plane conjugate to a detector and with the corneal conjugate plane replaced by a plane which is optically conjugate to the plane at which optical correction is to be effected. The detector in such a case can be an array responsive to the spatial location of an optical pattern, such as a CCD array or quadrant detector.

The foregoing and other objects, features and advantages of the invention will be apparent from the following description and from the accompanying drawings.

DESCRIPTION

Figure 1:
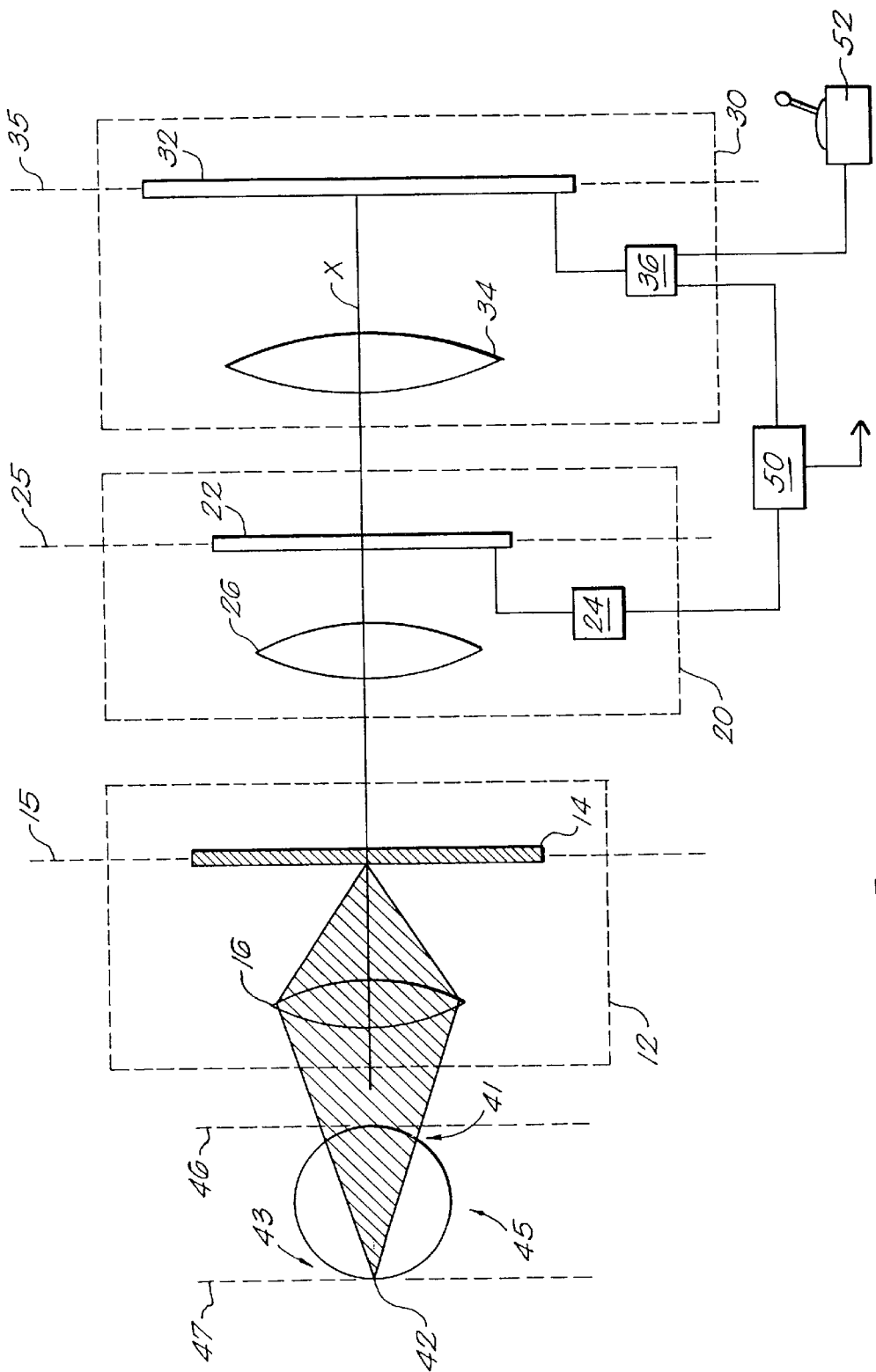
FIG. 1 shows a reference pattern being projected on the retina of an eye in a first embodiment of the invention.
Figure 2:
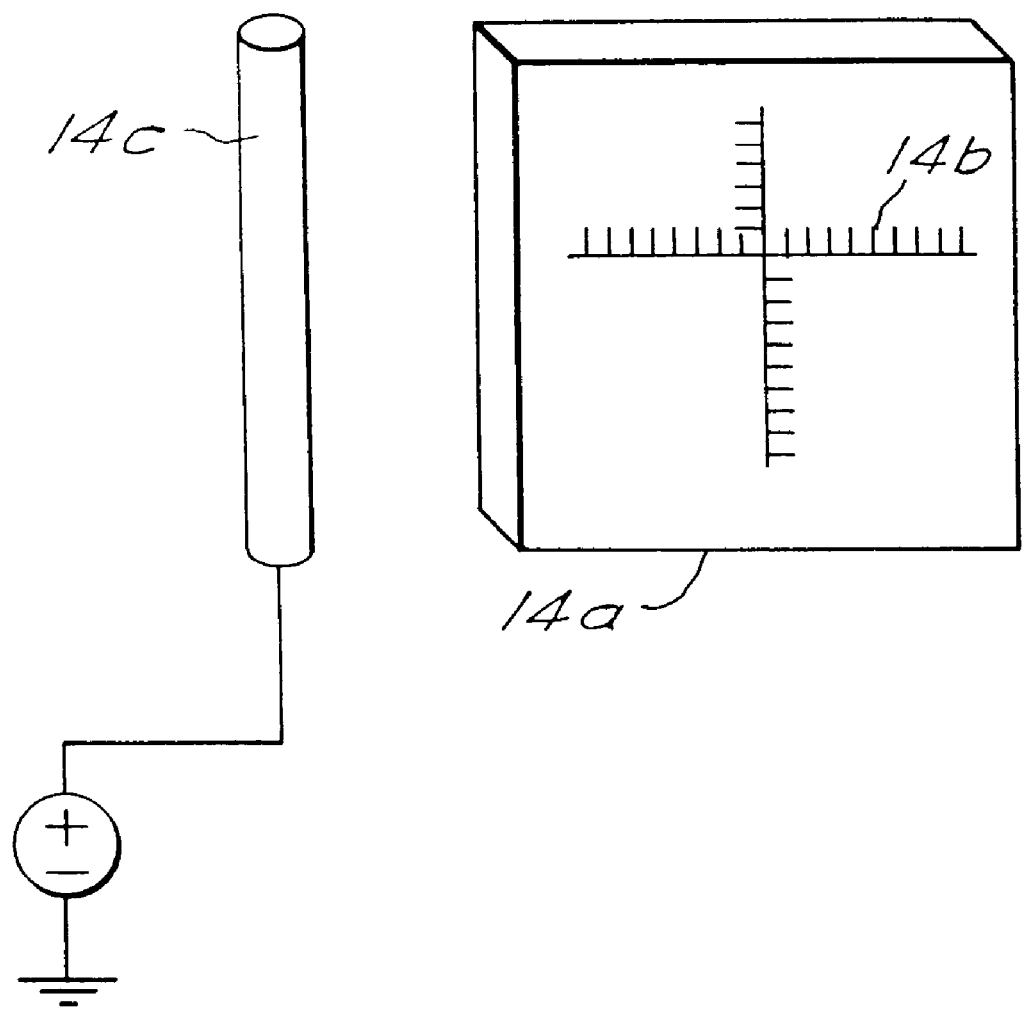
FIG. 2 is a perspective view of an illuminated reticle used to project the reference pattern in FIG. 1.
Figure 3:
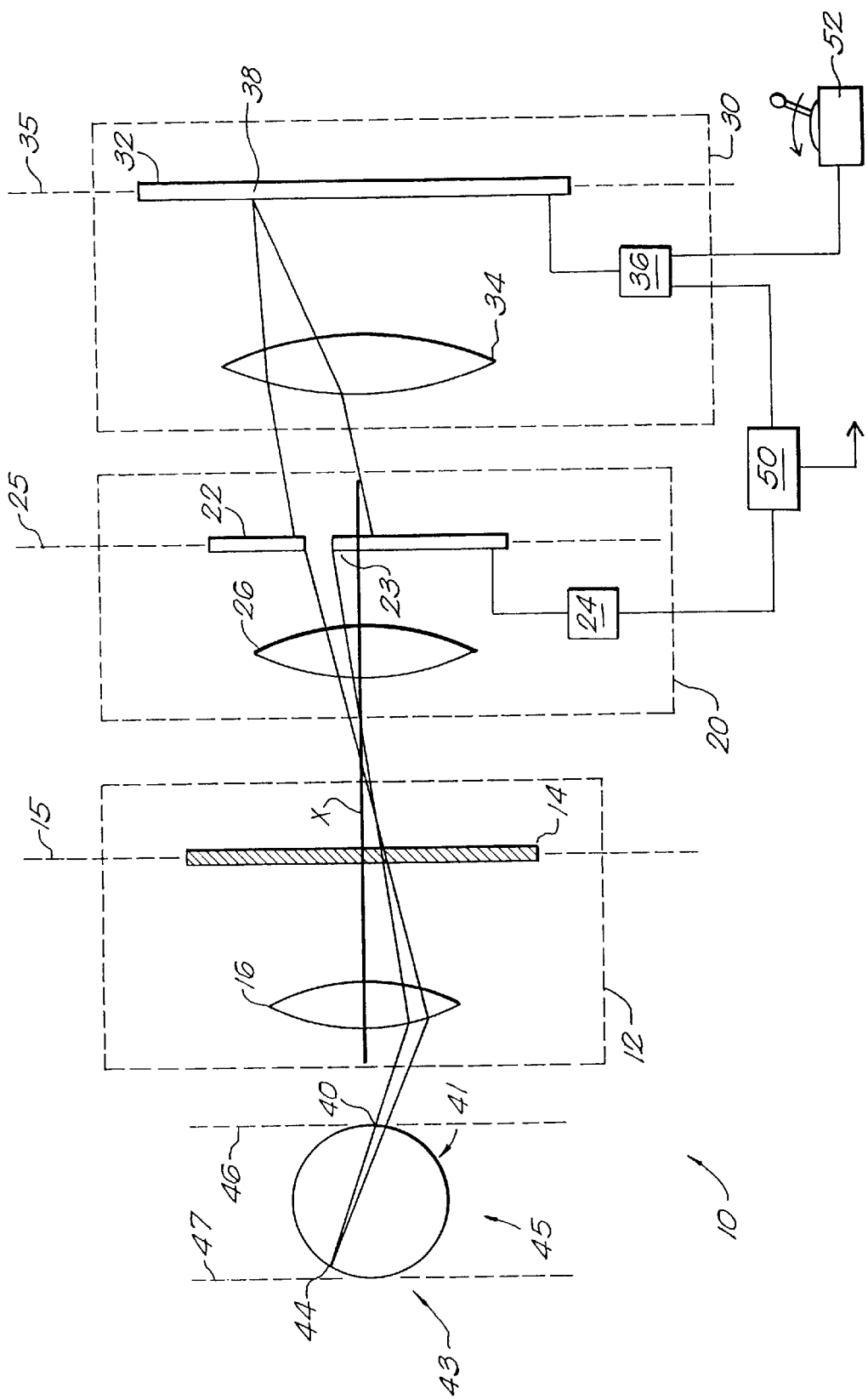
FIG. 3 shows a measurement pattern being projected on the retina of the eye in the embodiment depicted in FIG. 1.

In one embodiment, shown in FIGS. 1 and 3, a refractometer 10 according to the invention includes an illuminated reticle 14 coplanar with a reference plane 15 which is optically conjugate to a detector plane 47. A first lens 16 is disposed along the optical axis X between the illuminated reticle 14 and the eye 45. The illuminated reticle 14, shown in more detail in FIG. 2, can be a glass plate 14*a* having a cross or other reference mark 14*b* etched on the plate. The glass plate 14*a* is illuminated by a light source 14*c* adjacent to the plate. Together, the illuminated reticle 14 and the lens 16 form a reference optical subsystem 12.

The refractometer further includes a mask 22 coplanar with a site-selection plane 25 and disposed along the optical axis X. The mask 22 has a moveable site-selecting aperture 23 whose location in the site-selection plane 25 is controlled by an aperture controller 24. A second lens 26 is disposed along the optical axis X between the mask 22 and the illuminated reticle 14. Together, the mask 22 and the lens 26 form a site designator 20 for selecting a measurement site 40 on a measurement plane 46 optically conjugate to the site-selection plane 25.

Figure 6A:
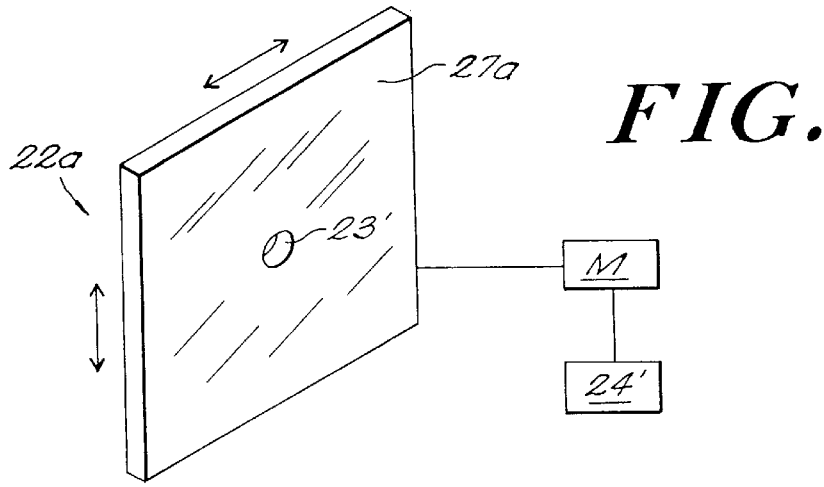
FIG. 6A shows the mask of FIGS. 1 and 3 implemented using an opaque screen and a stepping motor.

As shown in FIG. 6A, the mask 22 having a moveable site-selecting aperture 23 can be implemented by coupling a stepping motor M to both an aperture controller 24 and an opaque screen 27*a* having an aperture 23. In response to the aperture controller 24, the stepping motor M translates the opaque screen 27*a* in the site-selection plane 25, thereby translating the aperture 23 in the site-selection plane 25 as well.

Figure 6B:
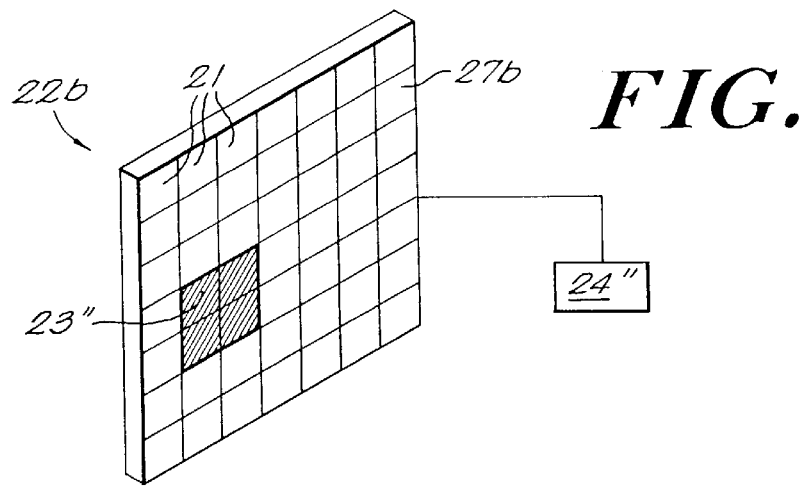
FIG. 6B shows the mask of FIGS. 1, 3, 4 and 5 implemented using a spatial light modulator.
Figure 6C:
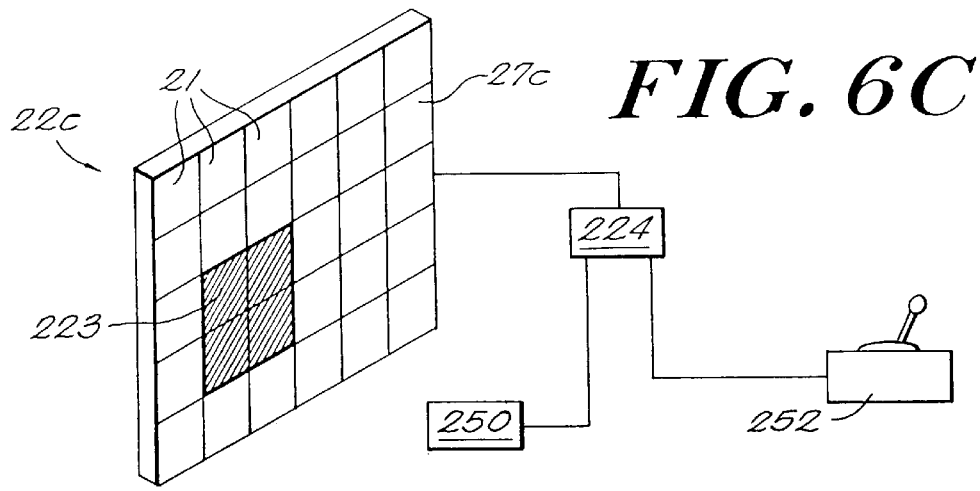

Alternatively, as shown in FIG. 6B, the mask 22 can be implemented by providing a spatial light modulator 27*b* having a multiplicity of light-modulating elements 21, each of which can be switched between an "ON" state and an "OFF" state. One or more light-modulating elements in the "ON" state can then form an aperture 23 whose size, shape, and location on the mask can be controlled by the distribution of light-modulating elements forming it. These light-modulating elements 21 can be liquid crystals, in which case the ON and OFF states correspond the transmissive and opaque states of the liquid crystal. Alternatively, the light-modulating elements 21 can be moveable micro-mirrors, in which case the ON state corresponds to the position in which the micro-mirror reflects light toward the proximal retinal plane 15 and the OFF state corresponds to the position in which the micro-mirror deflects light away from proximal retinal plane 15. It will be appreciated by those skilled in the art that other types of spatial light modulators can be used.

By implementing the mask 22 with a spatial light modulator 27*b* having individually addressable light-modulating elements 21, apertures 23 of different sizes and shapes can easily be formed. Moreover, a mask 22 implemented by a spatial light modulator 27*b* is not subject to mechanical vibration and inertia as is the mask 22 translated by a motor M as shown in FIG. 6A.

The refractometer shown in FIGS. 1 and 3 also includes an illumination pattern source 32 coplanar with an object plane 35 which is optically conjugate with the detector plane 46 and disposed along the optical axis X. An illumination controller 36 connected to the illumination pattern source 32 provides control of the pattern of illumination generated by the illumination source 38. A third lens 34 directs light form the illumination source 38 toward the mask 22. The illumination controller 36 is typically under control of the patient who can thereby select the location of the illumination source 38 within the object plane 35. The illumination controller 36, the third lens 34, and the illumination pattern source 32 form the measurement optical subsystem 30.

Figure 7A:
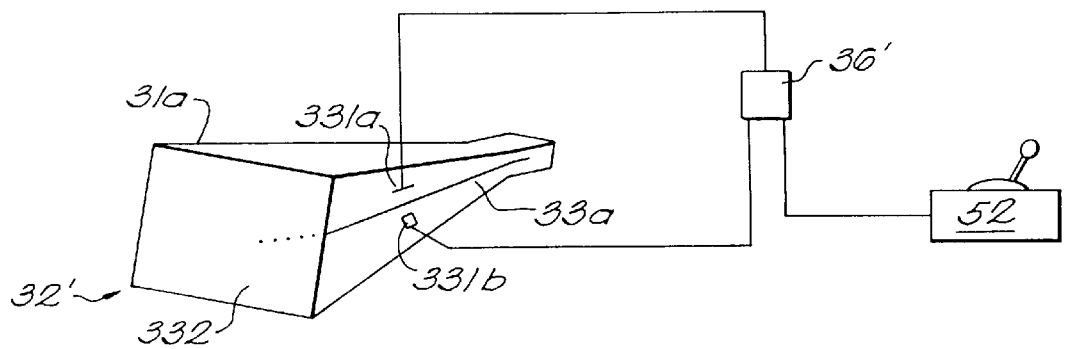
FIG. 7A shows an implementation of the illumination pattern source of FIGS. 1, 3, 4 and 5 as a cathode ray tube.
Figure 7B:
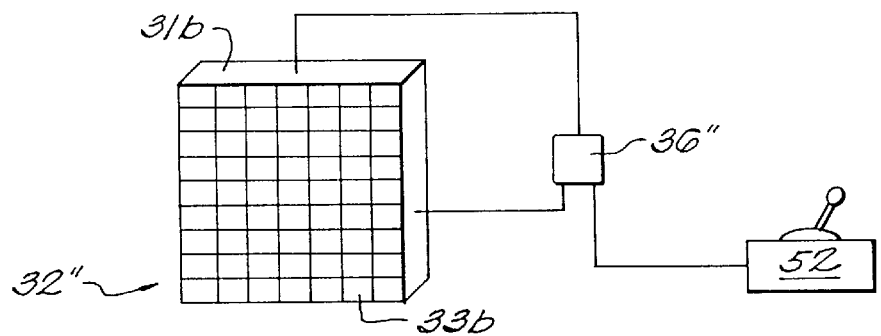
FIG. 7B shows an implementation of the illumination pattern source of FIGS. 1, 3, 4 and 5 as an array of light-emitting elements.
Figure 7C:
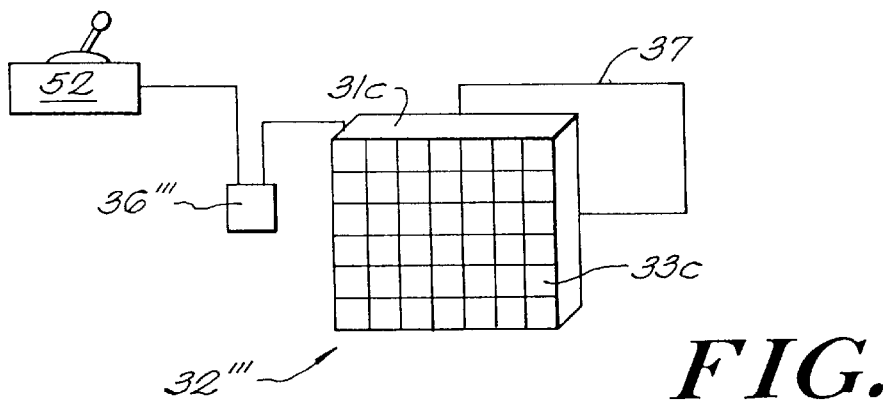
FIG. 7C shows an implementation of the illumination pattern source of FIGS. 1, 3, 4 and 5 as an array of light-modulating elements.

The illumination pattern source 32 can be implemented, as shown in FIG. 7A, with a cathode ray tube 31a in which the deflection of the electron beam 33a is under the control of the illumination controller 36. Alternatively, the illumination pattern source 32 can be implemented, as shown in FIG. 7B, with an array 31b of individually addressable light emitting elements 33b, such as light emitting diodes, in which case the illumination controller 36 controls which light emitting elements 33b are turned on. Conversely, as shown in FIG. 7C, the illumination pattern source 32 can include a uniform light source 37 distal to the distal retinal conjugate plane 35 and an array 31c of individually addressable light-modulating elements 33c at the distal retinal conjugate plane 35. In this case, the illumination controller 36 can control which light-modulating elements 33c will block light generated by the uniform light source 37.

Both the illumination controller 36 and the aperture controller 24 are connected to a processor 50 which can determine the normal vector to the optimal wavefront associated with each point on the cornea 41 on the measurement plane 46 in a conventional manner.

Referring to FIG. 1, light emitted by the illuminated reticle 14 at the proximal retinal conjugate plane 15 illuminates a lens 16 which focuses that light onto a reference pattern position 42 on the retina 43. This enables the patient to see a focused image of the reference mark 14b shown in FIG. 2.

Concurrently with the operation shown in FIG. 1, the aperture controller 24 moves the movable aperture 23 on the mask 22 to a designated location in the site-selection plane 25, as shown in FIG. 3. This can be achieved by either mechanically translating the mask 22 (see FIG. 6A) or, in the case of mask implemented by a spatial light modulator, by addressing selected light-modulating elements (see FIG. 6B). Movement of the aperture 23 across the site-selection plane 25 has the effect of choosing a measurement site 40 on the cornea 41 of the patient's eye 45.

Using the illumination controller 36, the patient can control the position of the illumination source 38 on the illumination pattern source 32. Light generated at the object plane 35 by the illumination source 38 crosses the site-selection plane 25 by passing through the aperture 23 in the mask 22. This light is then directed toward the selected measurement site 40 on the measurement plane 46 that corresponds to the location of the moveable aperture 23 in the site-selection plane 25. As is apparent from inspection of FIG. 3, light passing through the moveable aperture 23 crosses the measurement plane 46 at the selected measurement site 40 independent of the position of the illumination source 38 on the object plane 35.

In a perfect eye, light crossing the measurement plane 46 comes to a focus at a measurement pattern position 44 which is coincident with the reference pattern position 42. In an imperfect eye, that light is transmitted to a measurement pattern position 44 displaced from the reference pattern position 42. The measurement pattern position depends on the local properties of the selected measurement site 40 and on the angle of incidence of the incoming light ray. Consequently, the location of the measurement pattern position 44 on the retina 43 can be changed by changing the location of the illumination source 38 on the object plane 35.

What the patient sees when the refractometer 10 is in use is therefore a stationary image of the reference mark 14b at the reference pattern position 42 together with a moveable image of the illumination source 38 at the measurement pattern position 44.

To obtain a measure of the normal vector of the optimal wavefront associated with a selected measurement site 40, the aperture controller 24, under the control of the processor 50, moves the aperture 23 to a location which corresponds to the location of a selected measurement site 40. The patient then moves the location of the illumination source 38, perhaps with a joystick or similar device connected to the illumination controller 36, until the image of the illumination source on the measurement pattern position 44 coincides with the image of the reference pattern 14b on the reference pattern position 42.

By tracking the distance and the direction in which the patient moves the measurement pattern 38, the processor 50 can infer the normal vector of the optimal wavefront associated with the selected measurement site on the patient's eye. The processor 50, which is also in communication with the illumination controller 36, determines the magnitude and direction that the illumination source had to be moved in order to become aligned with the reference mark. This information enables the processor 50 to calculate, using conventional means, the normal vector of the optimal wavefront associated with the selected measurement site as well as a Seidel or polynomial expansion describing the optical system.

It will be appreciated, by one skilled in the art, that the foregoing apparatus and method for measuring the normal vector to the optimal wavefront at a selected measurement site on the cornea can also be used to measure the normal vector to the optimal wavefront at a selected measurement site on a non-living lens system. This can be accomplished by replacing the retina with a detector having a light sensing array, such as a CCD camera or a quadrant detector, and placing the pupil of the lens system at the measurement plane. Such an embodiment is shown in FIGS. 8 and 9.

Figure 8:
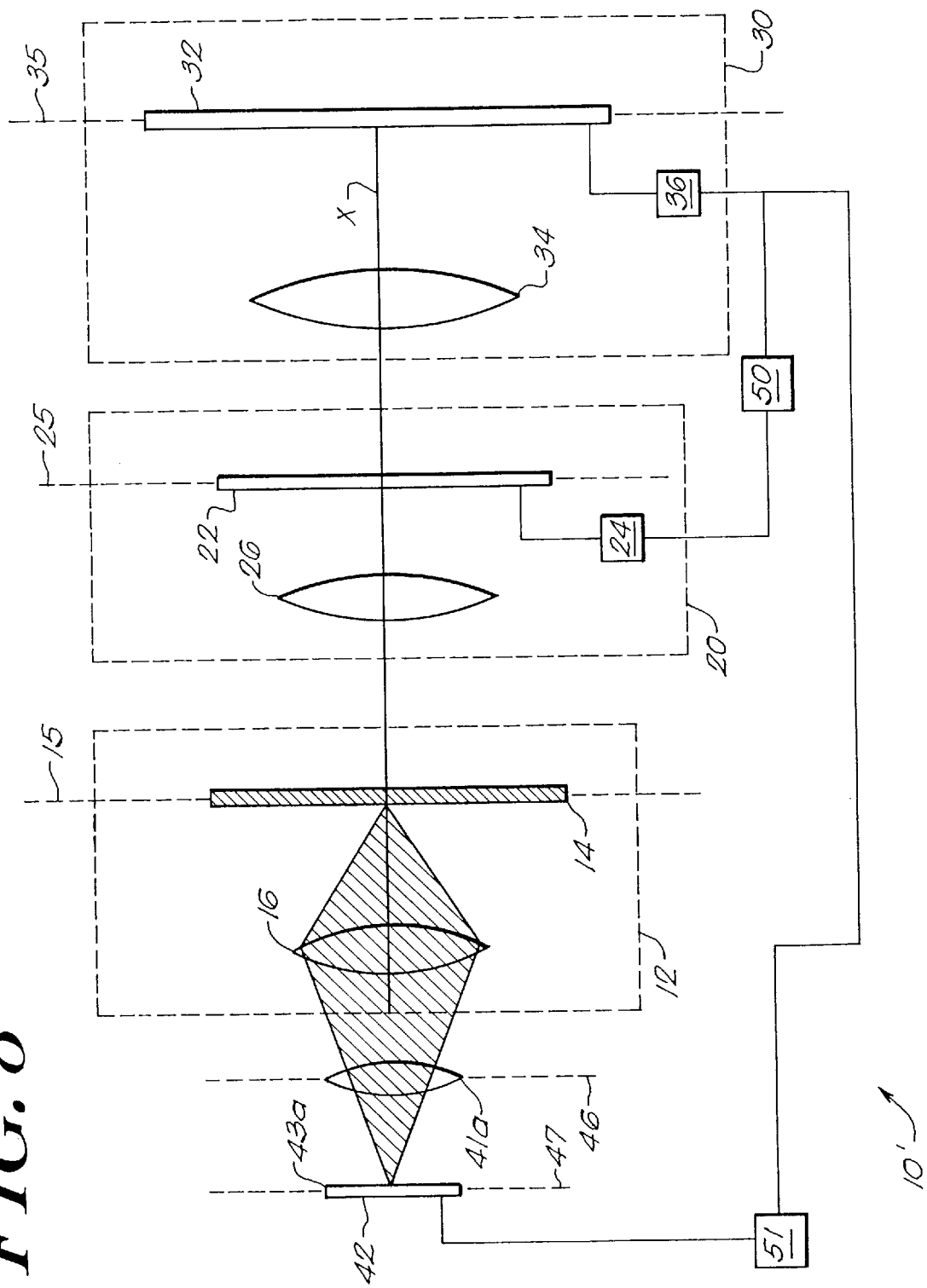
FIGS. 8–11 correspond to FIGS. 1, 3, 4 and 5 with the eye replaced by a lens system and with the retina of the eye replaced by a detector.
Figure 9:
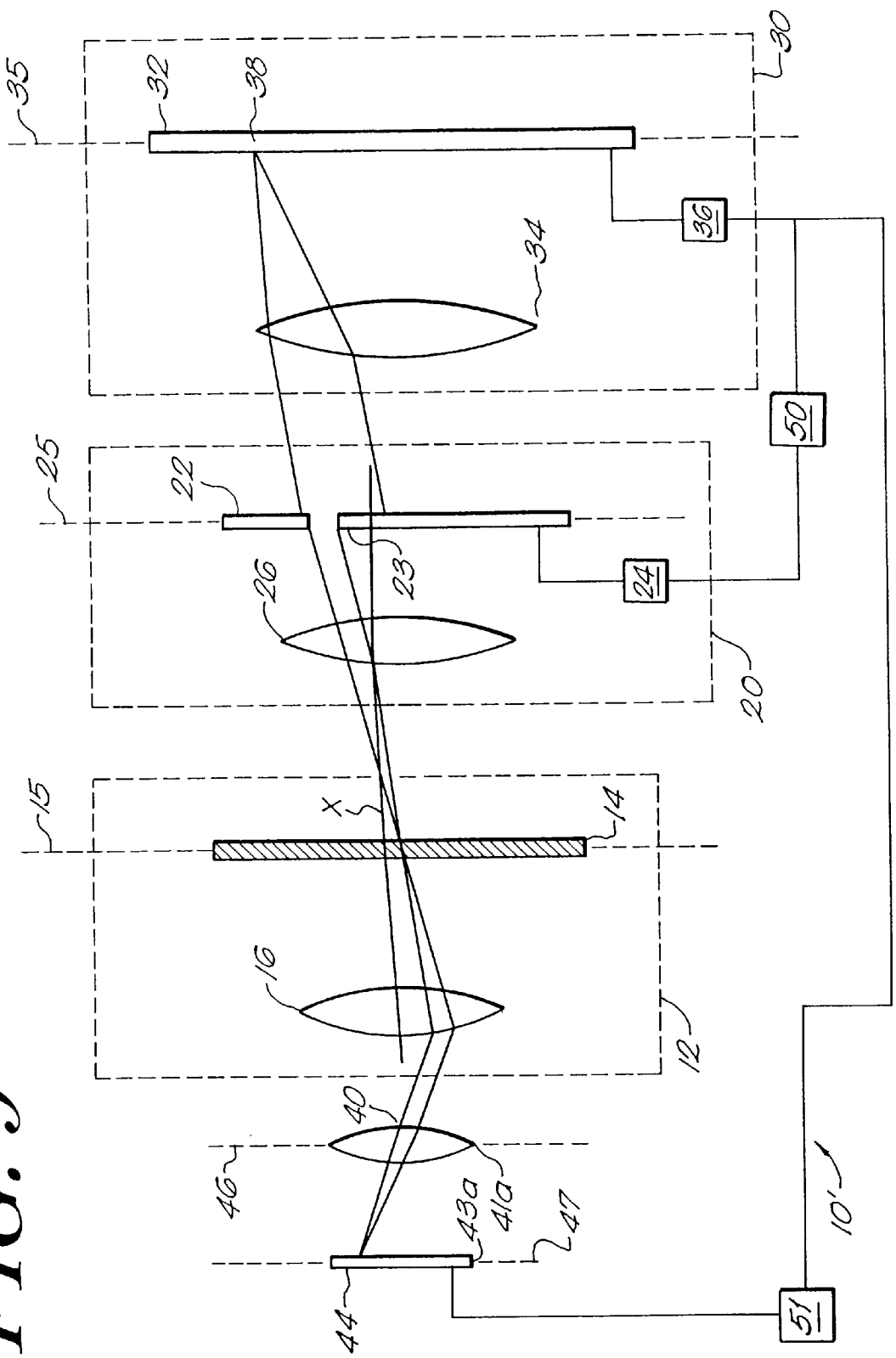

FIGS. 8 and 9 correspond to FIGS. 1 and 3 in which the cornea 41 is replaced by an optical system 41a whose optimal wavefront is sought and in which the retina 43 is replaced by a detector 43a which is responsive to the spatial location of an incident light source. The detector 43a is in communication with a processor 51 which, based on the difference between the location of the reference pattern position 42 and the location of the measurement pattern position 44, signals the illumination controller 36 to move the illumination source 38 so as to align the measurement pattern position 44 with the reference pattern position 42.

Figure 4:
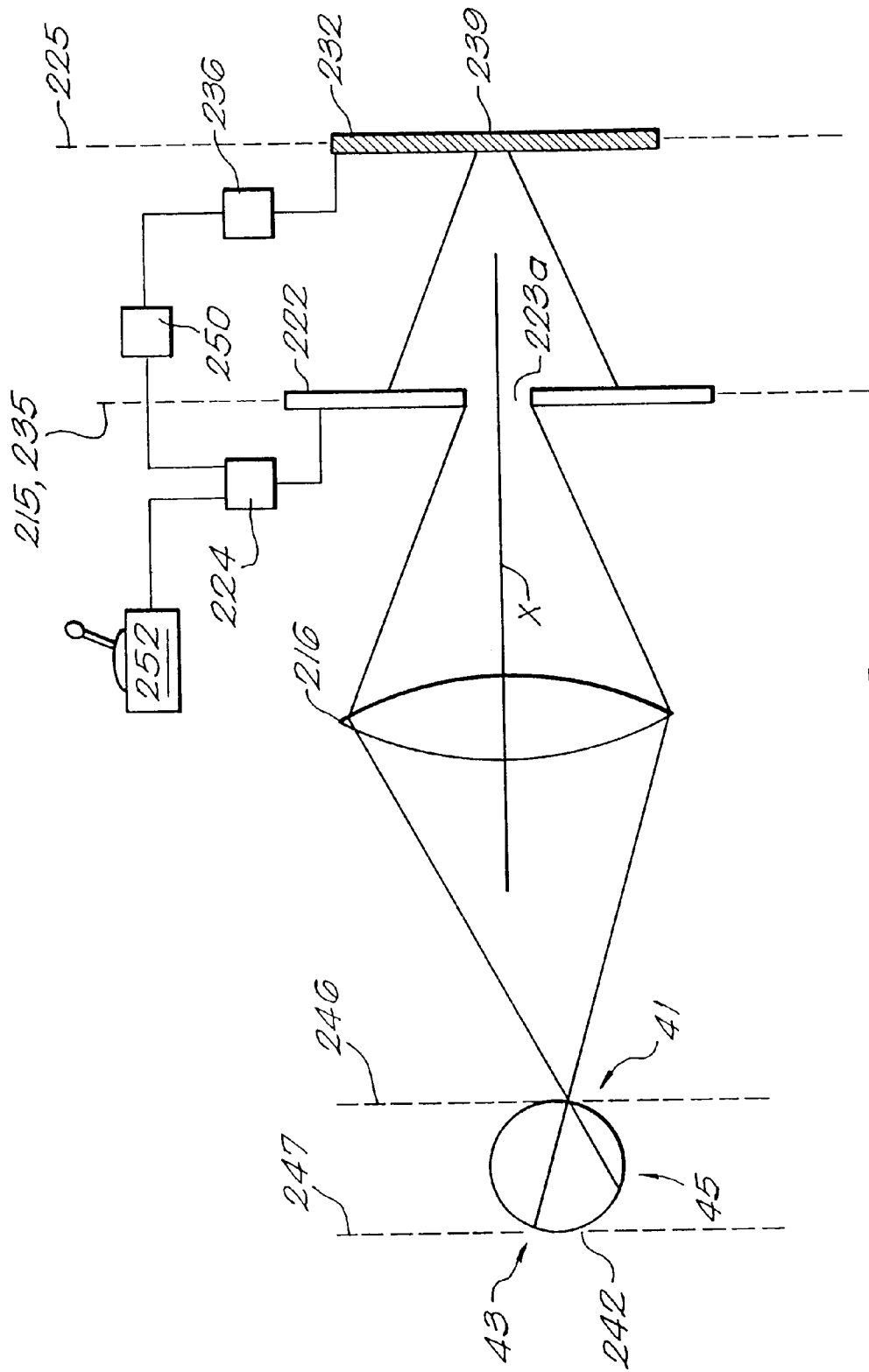
FIG. 4 shows a reference pattern being projected on the retina of an eye in a second embodiment of the invention.
Figure 5:
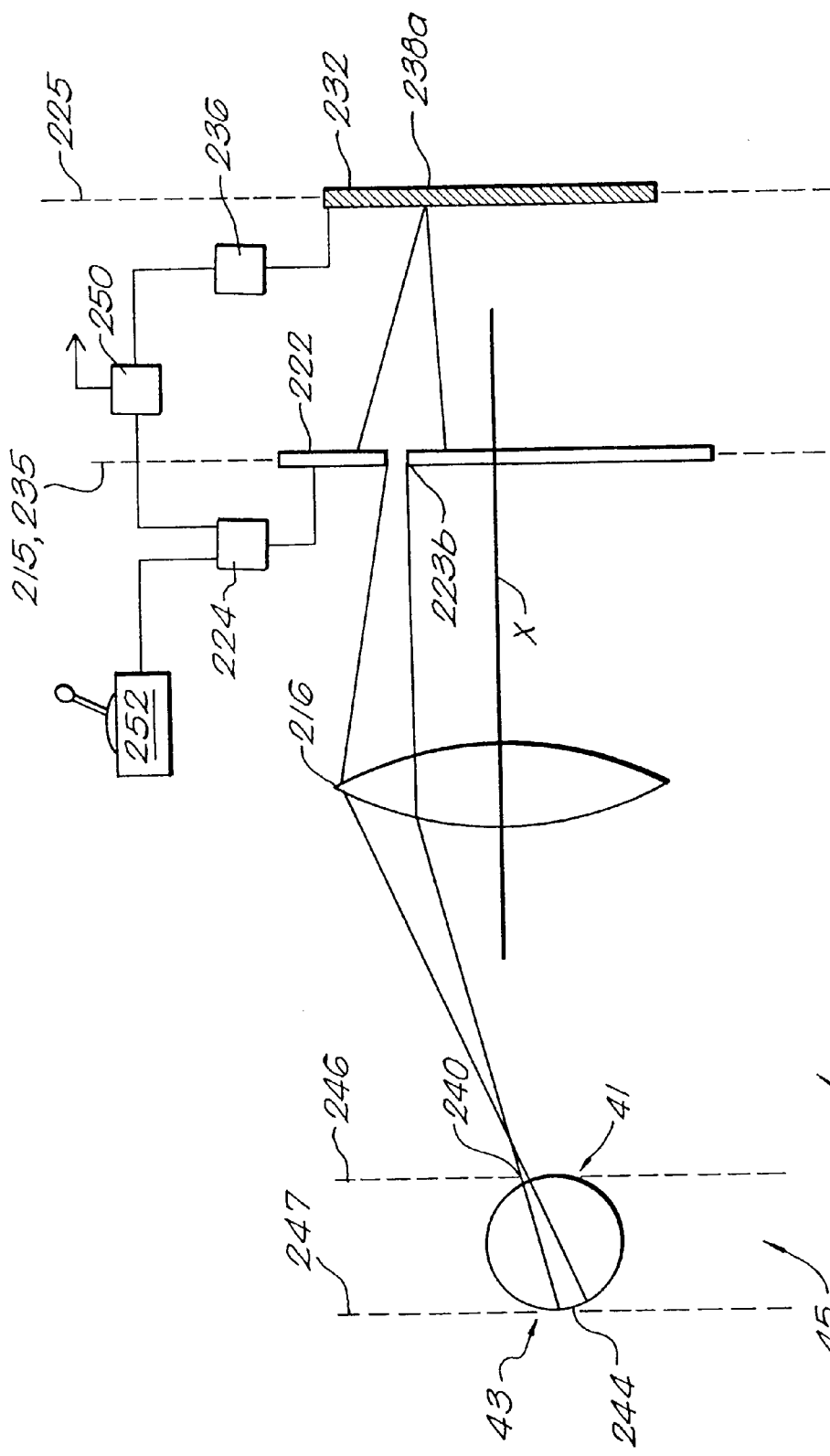
FIG. 5 shows a measurement pattern being projected on the retina of the eye in the embodiment depicted in FIG. 4.

In an alternative embodiment, shown in FIGS. 4 and 5, a refractometer 11 incorporating the invention includes an illumination pattern source 32 which is coplanar with a site-selection plane 25 instead of with an object plane. An illumination controller 36 connected to the illumination pattern source 32 provides control of the pattern of illumination generated by it. In this embodiment, it is the illumination pattern source 38 and the illumination controller 32 that form the site designator 20.

As shown in FIG. 5, the second embodiment, like the first embodiment, includes a mask 22 on the optical axis X. The mask 22 has a moveable aperture 23b whose location is controlled by an aperture controller 24. However, unlike the mask in the first embodiment, this mask 22 is coplanar not with a site-selection plane 25 but with the object plane 35. In this embodiment, therefore, the mask 22, the moveable measurement aperture 23b, and the aperture controller 24 form the measurement optical subsystem 30 and not the site designator 20. Because of its new function, this moveable aperture is now referred to as a moveable "measurement" aperture 23b to distinguish it from the moveable site-selecting aperture in FIG. 3.

Various implementations of the illumination pattern source 32 and of the mask 22 have already been described in connection with the first embodiment 10 of the refractometer. It is understood that the three specific implementations of the illumination pattern source 32 shown in FIGS. 7A–7C are applicable to this alternative embodiment 11 of the refractometer. For reasons that will be apparent from the following description of the operation of this refractometer 11, a mask 22 implemented by a spatial light modulator 27b, as shown in FIG. 6B, is preferable.

In operation, the refractometer 11 switches between operating in a reference mode, shown in FIG. 4, and operating in a measurement mode, shown in FIG. 5. During the reference mode, the refractometer 11 projects a reference pattern on the eye. During the measurement mode, the refractometer 11 projects a measurement pattern on the eye. The refractometer 11 alternates between operating in the measurement mode and operating in the reference mode rapidly enough so that, as a result of persistence of vision, the patient perceives the reference mark and the measurement pattern simultaneously.

When operating in the reference mode, shown in FIG. 4, the aperture controller 24, under the control of a processor 50, forms a reference aperture 23a in the shape of a reference pattern. Concurrently, the illumination controller 36, also under the control of the processor 50, generates a reference illumination pattern 39. Light from the reference illumination pattern 39 passes through the reference aperture 23a and, as a result of the location of the reference aperture 23a on the object plane 35, comes to a focus on a reference pattern position 42 on the retina 43. This results in the patient's perception of a reference mark during the period in which the refractometer 11 operates in the reference mode.

The reference illumination pattern 39 can be formed by a broad area on the illumination pattern source 32 as shown in FIG. 4. This will result in the patient perceiving a bright image of the reference pattern 14b. However, as a result of aberration introduced by the breadth of the reference illumination pattern 39, the reference pattern 14b will appear distorted. Alternatively, The reference illumination pattern 39 can be a small area (not shown) on the illumination pattern source 32, in which case the patient perceives a dim but sharp image of the reference mark 14b.

When operating in the measurement mode, shown in FIG. 5, the aperture controller 24 forms a moveable measurement aperture 23b on the mask 22 in the object plane 35. The location of this measurement aperture 23b is under the control of the patient. Concurrently, the illumination controller 36 generates a measurement pattern 38a on the illumination pattern source 32.

Light from the measurement pattern 38a passes through the measurement aperture 23b. Since this light originates on the site-selection plane 25, it comes to a focus on the measurement plane on which is disposed the cornea 41 of the patient's eye. Note that in this configuration, any light which leaks through the mask 22 originates on the object plane 35. Since this plane is conjugate to the retina, this leakage light comes to a focus on the retina 43 rather than on the cornea 41. As a result, such leakage light does not enlarge the selected measurement site 40 on the cornea. Because this leakage light manifests itself by a reduction in the contrast between the measurement pattern viewed by the patient and the background, it is readily distinguishable from the light passing through the aperture 23b. This is a particularly useful property since because of it, the light-modulating elements 21 in the spatial light modulators 27b used for implementing the mask 22 need not be perfectly opaque when operated in their "OFF" state.

Light from the measurement pattern 38a illuminates the retina 43 at a measurement pattern position 44, and results in the patient's perception of an image of the measurement pattern 38a at a measurement pattern position 44 of the retina. This measurement pattern position 44 is, in general, displaced from the location of the image of the reference mark 14b on the reference pattern position 42. The extent to which the measurement pattern position 44 is displaced from the reference pattern position 42 depends, in part, on the direction in which the light ray forming that image travels to the measurement plane 46. Because this direction depends on the location of the aperture 23b, and because the location of the aperture 23b is under the patient's control, the patient can align the measurement pattern 38a with the reference pattern in a manner similar to that described in connection with the first embodiment of the invention.

As the refractometer 11 switches between operating in reference mode and operating in measurement mode, the patient sees a stationary image of the reference mark 14b at the reference pattern position 42 followed by a moveable image of the illumination source 38 at the measurement pattern position 44. As a result of persistence of vision, the patient perceives these images simultaneously.

To determine the normal vector of the optimal wavefront at a selected measurement site 40 on the measurement plane 46, the illumination controller 36, under the control of the processor 50, moves the measurement pattern 38a to a location which corresponds to the location of a selected measurement site 40. The patient then moves the location of the moveable measurement aperture 23b, perhaps with a joystick or similar device connected to the aperture controller 24, until the image of the measurement pattern 38a on the measurement pattern position 44 coincides with the image of the reference mark 14b on the reference pattern position 42. By tracking the distance and the direction in which the patient moves the moveable measurement aperture 23b, the processor 50 can evaluate the normal vector of the optimal wavefront associated with the selected measurement site 40 on the patient's eye.

It will be appreciated by those skilled in the art that this second embodiment can likewise be modified for determining the normal vector of the optimal wavefront associated with a lens or other refractive surface. For example, FIGS. 10 and 11 correspond to FIGS. 4 and 5 in which the measurement plane 46 is coplanar with the pupil 41a of a lens system whose optimal wavefront is sought and in which the retina 43 is replaced by a detector 43a which is responsive to the spatial location of an incident light source. The detector 43a is in communication with a processor 51 which, based on the difference between the location of the reference pattern position 42 and the location of the measurement pattern position 44, signals the aperture controller 24 to move the measurement aperture 23b so as to align the measurement pattern position 44 with the reference pattern position 42.

Figure 10:
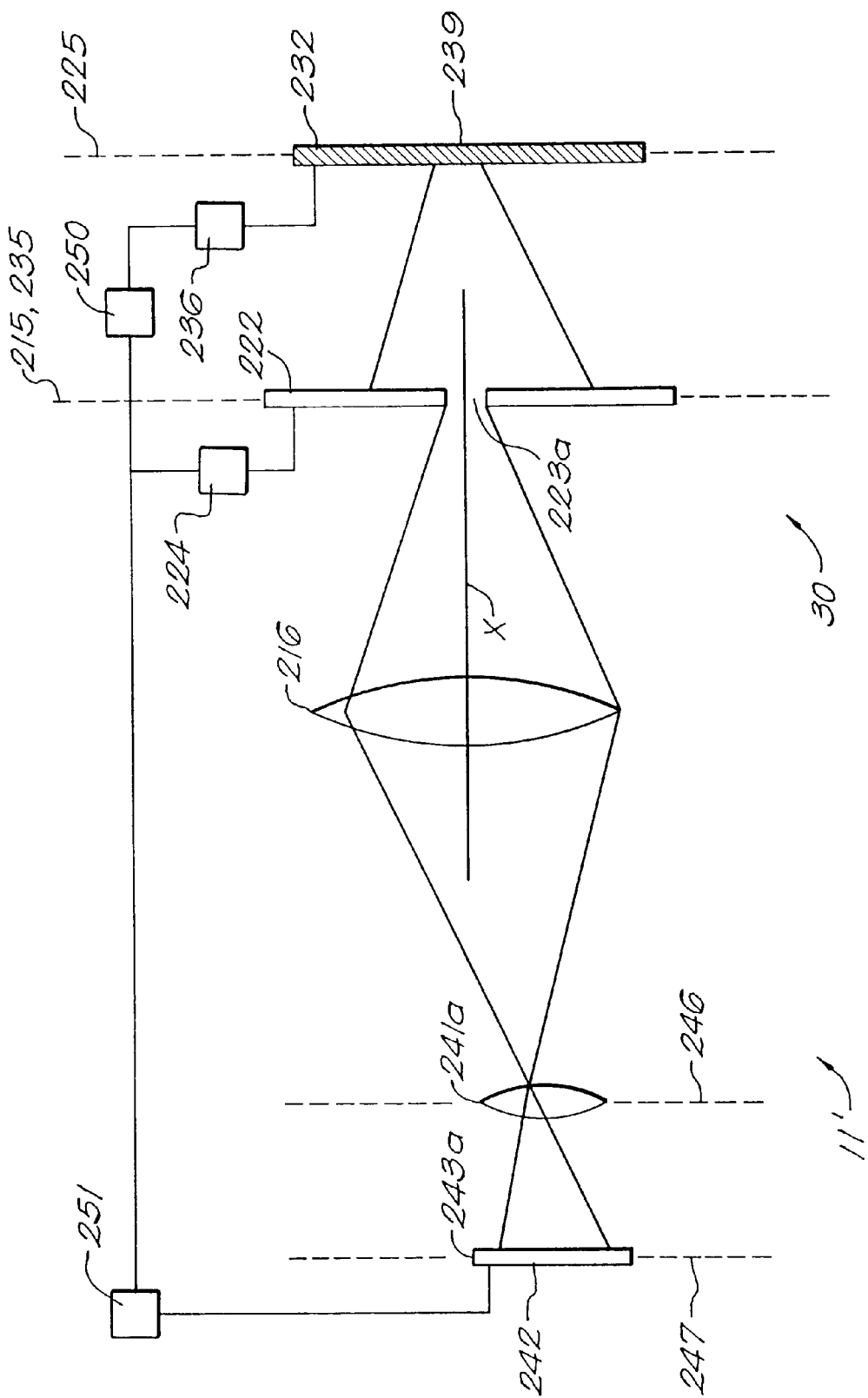
Figure 11:
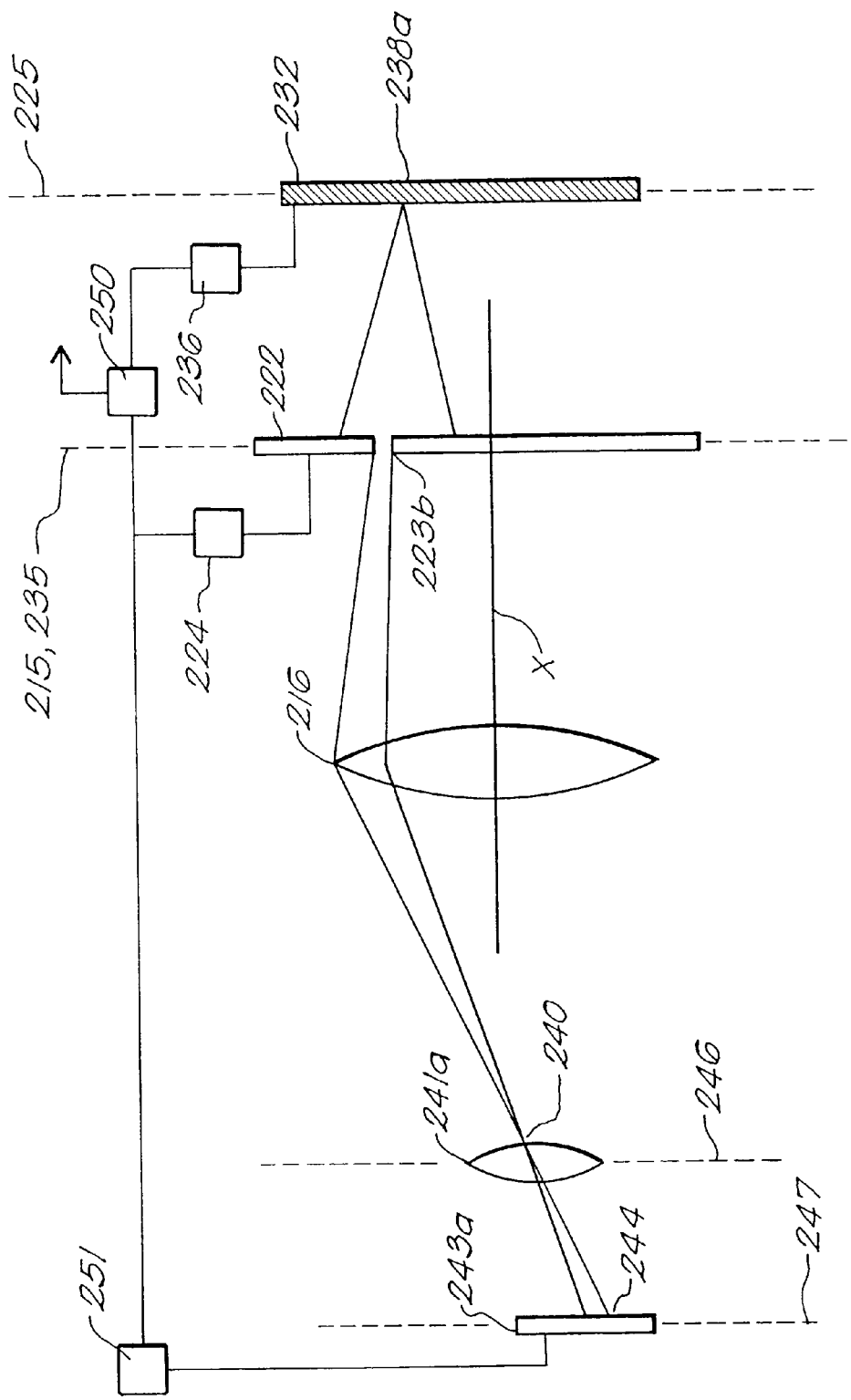
Figure 12A:
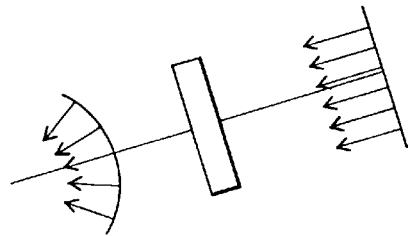
FIG. 12A shows an ideal optical system which transforms a planar wavefront into a spherical wavefront.
Figure 12B:
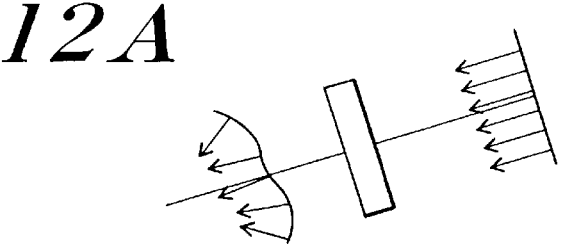
FIG. 12B shows an optical system which transforms a planar wavefront into an irregular wavefront.
Figure 12C:
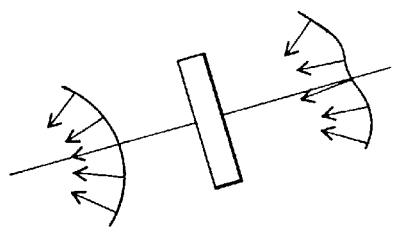
FIG. 12C shows the optical system of FIG. 12B transforming its optimal wavefront into a spherical wavefront such as that shown in FIG. 12A.
Figure 13:
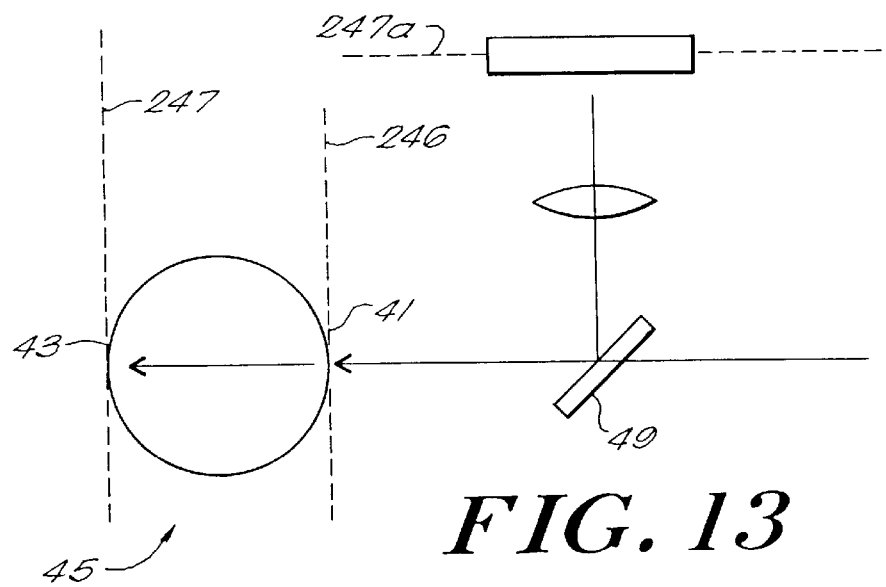
FIG. 13 shows a beamsplitter and lend used to transmit the reference pattern and measurement pattern at the retina of an eye to a detector.

The addition of a beamsplitter 49, as shown in FIG. 13, enables the processor 51 shown in FIGS. 10 and 11 to be used for determining the optimal wavefront at the cornea. The beasmplitter 49 is placed in the optical path between the measurement plane 46 and the site-selection plane 25. The beamsplitter 49 transmits a first portion of the light incident on it through the measurement plane to the retina 43. Light re-emerging from the lens system, scattered or reflected from the retina or other structure 43, is, in part, reflected by the beamsplitter to a detector 43a located on a plane conjugate to the retina. The detector 43a is in communication with a processor 51 as described above. Based on the difference between the location of the reference pattern position 42 and the location of the measurement pattern position 44, the processor 51 signals the aperture controller 24 to move the measurement aperture 23b so as to align the measurement pattern position 44 with the reference pattern position 42. This feature is especially useful when a patient, such as a small child, cannot align the reference pattern position 42 with the measurement pattern position 44.

It will thus be seen that the invention efficiently attains the objects set forth above. Since certain changes may be made in the above constructions without departing from the scope of the invention, it is intended that all matter contained in the above description or shown in the accompanying drawings be interpreted as illustrative and not in a limiting sense.

It is also to be understood that the following claims are intended to cover all generic and specific features of the invention described herein, and all statements of the scope of the invention which as a matter of language might be said to fall there between.

Having described the invention, what is claimed as new and secured by Letters Patent is:

1. A refractometer for determining the optimal wavefront at a measurement plane, said refractometer comprising
    a first spatial light pattern generator disposed at a first plane, said first plane being optically conjugate to said measurement plane,
    a second spatial light pattern generator coaxial with said first spatial light pattern generator, said second spatial light pattern generator disposed at a second plane optically conjugate to a detector plane,
    control means coupled to said first and second spatial light pattern generators for operating said refractometer in
        a measurement interval during which a measurement pattern is projected through a selected measurement site on said measurement plane and onto a measurement pattern position on said detector plane, and
        a reference interval during which a reference pattern is projected through a selected reference site on said measurement plane and onto a reference pattern position on said detector plane, and
    alignment means for controlling an angle at which said measurement pattern is projected through said selected measurement site during said measurement interval.

2. The refractometer of claim 1 wherein said control means comprises means for operating said refractometer such that said measurement interval and said reference interval are successive intervals.

3. The refractometer of claim 1 wherein said control means comprises means for operating said refractometer such a that said measurement interval is contemporaneous with said reference interval.

4. The refractometer of claim 1 further comprising reference target projection means coaxial with said first spatial light pattern generator for generating, on a plane optically conjugate to said detector plane, a reference pattern.

5. The refractometer of claim 4 wherein said reference target projection means comprises
    a reference target disposed at a reference plane optically conjugate to said detector plane, and
    a reference light source illuminating said reference target.

6. The refractometer of claim 5 wherein said reference plane is coplanar with said second plane.

7. The refractometer of claim 5 wherein said reference plane is disposed between said second plane and said detector plane.

8. The refractometer of claim 5 wherein said reference target comprises a reticle disposed at said reference plane.

9. The refractometer of claim 4 wherein said reference target projection means comprises
    means forming an aperture in said second spatial light pattern generator,
    illumination means for generating light passing through said aperture, and
    means for coordinating the operation of said aperture forming means and said illumination means.

10. The refractometer of claim 1 further comprising site-selection means for selecting said measurement site.

11. The refractometer of claim 10 wherein said site-selection means comprises
    means for forming a site-selection light source in said first plane, and
    means for moving said site-selection light source to a selected point on said first plane.

12. The refractometer of claim 11 wherein said means for forming a moveable site-selection light source comprises
    a cathode ray tube illuminated by a beam, said cathode ray tube disposed coplanar with said first plane, and
    means for controlling the location of said beam on said cathode ray tube.

13. The refractometer of claim 11 wherein said means for forming a moveable site-selection light source comprises
    an array of light-emitting elements disposed coplanar with said first plane, each of said light-emitting elements having an active state in which it emits light and a darkened state in which it does not emit light, and
    means for selectively addressing said light-emitting elements.

14. The refractometer of claim 10 wherein said site-selection means comprises
    means for forming a moveable site-selection aperture in said first plane, and
    means for passing light through said site-selection aperture.

15. The refractometer of claim 14 wherein said means for forming a moveable site-selection aperture comprises
    an opaque screen disposed coplanar with said first plane, said opaque screen having a site-selection aperture therethrough, and
    means for moving said opaque screen, thereby moving said site-selection aperture in said first plane.

16. The refractometer of claim 14 wherein said means for forming a moveable site-selection aperture comprises
    an array of light-modulating elements disposed coplanar with said first plane, each of said light modulating elements having an ON state and an OFF state, and
    means for switching selected light-modulating elements from said array between said ON state and said OFF state, thereby forming a moveable site-selection aperture in said first plane.

17. The refractometer of claim 1 wherein said alignment means comprises a measurement light source moveable in said first plane, and means for controlling the location of said light source within said first plane.

18. The refractometer of 17 wherein said measurement light source comprises an array of light-modulating elements disposed coplanar with said first plane, each of said light modulating elements having an ON state and an OFF state, and said location control means comprises means for switching selected light-modulating elements from said array between said ON state and said OFF state, thereby forming a moveable site-selection aperture in said first plane.

19. The refractometer of claim 17 wherein said measurement light source comprises a cathode ray tube illuminated by a beam, said cathode ray tube disposed coplanar with said first plane, and said location control means comprises means for controlling the location of said beam on said cathode ray tube.

20. The refractometer of claim 17 wherein said alignment means comprises an array of light-emitting elements disposed coplanar with said first plane, each of said light-emitting elements having an active state in which it emits light and a darkened state in which it does not emit light, and means for selectively addressing said light-emitting elements.

21. The refractometer of claim 1 wherein said control means further comprises means for repeating said reference interval and said measurement interval.

22. The refractometer of claim 1 further comprising detector means disposed on a plane optically conjugate to said second plane to receive light from said site-selection plane, said detector being responsive to the spatial location of an incident light source.

23. The refractometer of claim 22 wherein said detector plane is coaxial with said measurement plane.

24. The refractometer of claim 22 wherein said alignment means further comprises means for receiving a signal from said detector means and means for responding to said signal by aligning said reference pattern position with said measurement pattern position.

25. The apparatus of claim 22 wherein said plane on which said detector is disposed is coplanar with said detector plane.

26. The apparatus of claim 22 further comprising a beamsplitter disposed between said second plane and said measurement plane to direct a first beam toward said detector plane and a second beam re-emegent from the lens system toward said detector.

27. A refractometer for determining the optimal wavefront at a measurement plane, said refractometer comprising means for generating a spatially varying optical pattern, said optical pattern being disposed at a first plane optically conjugate to said measurement plane, means for modulating said spatially varying optical pattern, said modulating means being disposed coaxially with said pattern generating means on a second plane optically conjugate to a detector plane, control means coupled to said pattern generating means and said pattern modulating means for operating said refractometer in a measurement interval during which a measurement pattern is projected through a selected measurement site on said measurement plane and onto a measurement pattern position on said detector plane, and a reference interval during which a reference pattern is projected through a selected reference site on said measurement plane and onto a reference pattern position on said detector plane, alignment means for controlling the angle at which said measurement pattern is projected through said selected measurement site during said measurement interval.

28. A method for determining the optimal wavefront at a measurement plane, said method comprising the steps of providing a first spatial light pattern generator disposed at a first plane, said first plane being optically conjugate to said measurement plane, providing a second spatial light pattern generator coaxial with said first spatial light pattern generator, said second spatial light pattern generator disposed at a second plane optically conjugate to a detector plane, projecting a measurement pattern through a selected measurement site on said measurement plane and onto a measurement pattern position on said detector plane during a measurement interval, projecting a reference pattern through a reference pattern site on said measurement plane and onto a reference pattern position on said detector plane during a reference interval, and aligning said measurement pattern position with said reference pattern position on said detector plane.

29. The method of claim 28 wherein said step of projecting said measurement pattern follows said step of projecting said reference pattern.

30. The method of claim 28 wherein said step of projecting said measurement pattern and said step of projecting said reference pattern occur contemporaneously.

31. The method of claim 28 wherein said step of projecting a reference pattern further comprises the step of generating, on a plane optically conjugate to said detector plane, a reference pattern.

32. The method of claim 31 wherein said step of generating a reference pattern comprises the step of illuminating a reference target disposed at a reference plane optically conjugate to said detector plane.

33. The method of claim 32 further comprising the step of positioning said reference plane to be coplanar with said second plane.

34. The method of claim 32 further comprising the step of positioning said reference plane between said second plane and said detector plane.

35. The method of claim 31 wherein said step of projecting a reference pattern comprises the steps of forming an aperture in a second spatial light pattern generator disposed at a plane optically conjugate to said detector plane, and passing light through said aperture.

36. The method of claim 28 further comprising the step of selecting said measurement site.

37. The method of claim 36 wherein said step of selecting said measurement site comprises the steps of forming a site-selection light source in a first plane conjugate to said measurement plane, and moving said site-selection light source to a selected point on said first plane.

38. The method of claim 37 wherein said step of forming a moveable site-selection light source comprises the step of controlling the location of a beam on a cathode ray tube illuminated by said beam, said cathode ray tube disposed coplanar with said first plane.

39. The method of claim 37 wherein said step of forming a moveable site-selection light source comprises the step of
selectively addressing said light-emitting elements from an array of light-emitting elements disposed coplanar with said first plane, each of said light-emitting elements having an active state in which it emits light and a darkened state in which it does not emit light.

40. The method of claim 36 wherein said step of selecting said measurement site comprises the steps of
forming a moveable site-selection aperture in said first plane, and
passing light through said site-selection aperture.

41. The method of claim 40 wherein said step of forming a moveable site-selection aperture comprises the step of
moving an opaque screen disposed coplanar with said first plane in a direction coplanar with said first plane, said opaque screen having a site-selection aperture therethrough.

42. The method of claim 40 wherein said step of forming a moveable site-selection aperture comprises the steps of
providing an array of light-modulating elements disposed coplanar with said first plane, each of said light modulating elements having an ON state and an OFF state, and
switching selected light-modulating elements from said array between said ON state and said OFF state, thereby forming a moveable site-selection aperture in said first plane.

43. The method of claim 28 wherein said aligning step comprises the step of
controlling the location of a measurement light source within said first plane.

44. The method of claim 43 wherein said controlling step comprises the steps of
providing an array of light-modulating elements disposed coplanar with said first plane, each of said light modulating elements having an ON state and an OFF state, and
switching selected light-modulating elements from said array between said ON state and said OFF state, thereby forming a moveable site-selection aperture in said first plane.

45. The method of claim 43 wherein said controlling step comprises the steps of
providing a cathode ray tube illuminated by a beam, said cathode ray tube disposed coplanar with said first plane, and
controlling the location of said beam on said cathode ray tube.

46. The method of claim 43 wherein said aligning step comprises the steps of
providing an array of light-emitting elements disposed coplanar with said first plane, each of said light-emitting elements having an active state in which it emits light and a darkened state in which it does not emit light, and
selectively addressing said light-emitting elements.

47. The method of claim 28 further comprising the step of
detecting, at the detector plane, the spatial location of an incident light source.

48. The method of claim 47 wherein said detecting step includes the step of providing a CCD array.

49. The method of claim 47 wherein said detecting step includes the step of providing a quadrant detector.

50. A refractometer for determining the normal vector to a wavefront at a selected measurement site on a cornea of a patient, said refractometer comprising
reference projection means coaxial with an optical axis for projecting, onto a reference pattern position on a retina of a patient, a reference pattern,
site-selection means, coaxial with said optical axis, for selecting said selected measurement site,
measurement projection means, coaxial with said optical axis, for projecting a measurement pattern through said selected measurement site for refraction to a measurement pattern position on said retina, and
alignment means for changing the location of said measurement pattern position, said alignment means permitting alignment of said measurement pattern position with said reference pattern position.

51. A refractometer for determining the optimal wavefront at a measurement plane, said refractometer comprising
pattern generating means for generating a spatially varying optical pattern, said optical pattern being disposed at a first plane conjugate to a detector plane,
pattern modulating means for modulating said spatially varying optical pattern, said pattern modulating means being disposed coaxially with said pattern generating means on a second plane optically conjugate to said measurement plane,
control means coupled to said first and second spatial light pattern generators for operating said refractometer in
a measurement interval during which a measurement pattern is projected through a selected measurement site on said measurement plane and onto a measurement pattern position on said detector plane, and
a reference interval during which a reference pattern is projected through a selected reference site on said measurement plane and onto a reference pattern position on said detector plane, and
alignment means for controlling an angle at which said measurement pattern is projected through said selected measurement site during said measurement interval.

* * * * *

UNITED STATES PATENT AND TRADEMARK OFFICE
CERTIFICATE OF CORRECTION

PATENT NO. : 6,000,800
DATED : December 14, 1999
INVENTOR(S) : Webb et al.

It is certified that error appears in the above-identified patent and that said Letters Patent is hereby corrected as shown below:

Column 1,
Line 3, the following two sentences should be inserted:
-- STATEMENT OF RIGHTS
This invention was made with government support under Grant DE-FG 02-91ER61229 awarded by the Department of Energy. The Government has certain rights in the invention. --

Signed and Sealed this

Seventh Day of October, 2003

JAMES E. ROGAN
*Director of the United States Patent and Trademark Office*